United States Patent [19]

Weitz et al.

[11] 4,042,588
[45] Aug. 16, 1977

[54] MANUFACTURE OF 1,2,4-DIHYDROTRIAZINE-4-OXIDE-SPIRO-(3,1′)-[OXIMINO-(2′)-CYCLOALKANES]

[75] Inventors: Hans-Martin Weitz, Bad Duerkheim; Rolf Fischer, Heidelberg; Dieter Lenke, Ludwigshafen, all of Germany

[73] Assignee: BASF Aktiengesellschaft, Ludwigshafen, Germany

[21] Appl. No.: 691,226

[22] Filed: June 1, 1976

[30] Foreign Application Priority Data

June 25, 1975 Germany ............................. 2528285

[51] Int. Cl.² .......................................... C07D 253/08
[52] U.S. Cl. .................................... 544/183; 424/249

[58] Field of Search ................................. 260/248 AS

[56] References Cited

U.S. PATENT DOCUMENTS 3,910,909  10/1975  Draber et al. ................. 260/248 AS Primary Examiner—John M. Ford
Attorney, Agent, or Firm—Keil, Thompson & Shurtleff

[57] ABSTRACT 1,2,4-Dihydrotriazine-4-oxide-spiro-(3,1′)-[oximino-(2′)-cycloalkanes] are manufactured by reaction of oximinocycloalk-1-enes, substituted in the 1-position, with hydrazine. The products, especially the triazine derivative described in Example 1, possess antiphlogistic properties and are starting materials for the manufacture of dyes and pharmaceuticals.

7 Claims, No Drawings

MANUFACTURE OF 1,2,4-DIHYDROTRIAZINE-4-OXIDE-SPIRO-(3,1')-[OXIMINO-(2')-CYCLOALKANES]

The present invention relates to a novel process for the manufacture of 1,2,4-dihydrotriazine-4-oxide-spiro-(3,1')-[oximino-(2')cycloalkanes] by reaction of oximino-cycloalk-1-enes, which are substituted in the 1-position, with hydrazine.

The formation of 1,2,4-triazine-1-oxides by oxidation of substituted 1,2,4-triazines has been disclosed (J. Org. Chem., 36 (1971), 787–790). However, 1,2,4-triazine-4-oxides cannot be prepared by this method.

It is an object of the present invention to provide a new process for making 1,2,4-dihydrotriazine-4-oxide-spiro-(3,1')-[oximino-(2')cycloalkanes] in a one-step reaction, in a simple and economical manner and in good yield and high purity.

The new 1,2,4-dihydrotriazine-4-oxide-spiro-(3,1')-[oximino-(2')cycloalkanes] are a further object of the present invention.

We have found that these objects are achieved and that 1,2,4-dihydrotriazine-4-oxide-spiro-(3,1')-[oximino-(2')-cycloalkanes] of the formula

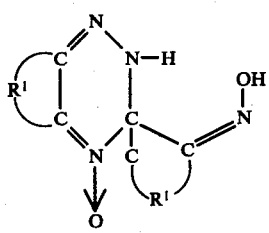

where R¹ is an aliphatic radical, are obtained in an advantageous manner, when oximino-cycloalk-1-enes, which are substituted in the 1-position, of the formula

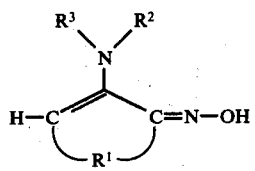

where R² and R³ are identical or different and each is an aliphatic radical, or R² and R³ together with the adjacent nitrogen are members of a heterocyclic ring, and R¹ is an aliphatic radical, are reacted with hydrazine in organic solvents which are inert under the reaction conditions.

Where 1-morpholino-6-oximino-cyclohex-1-ene is used, the reaction can be represented by the following equation:

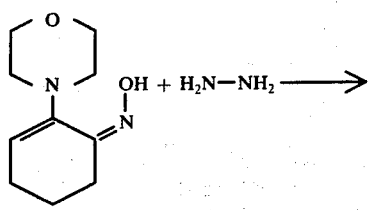

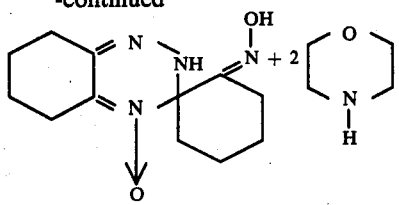

The process of the invention gives 1,2,4-dihydrotriazine-4-oxide-spiro-(3,1')-[oximino-(2')-cycloalkanes] in a one-step reaction, in a simple and economical manner and in good yield and high purity.

Preferred starting materials II and accordingly preferred end products I are those where R² and R³ are identical or different and each is alkyl of 1 to 8 carbon atoms or R² and R³ together with the adjacent nitrogen are members of a 5-membered or 6-membered heterocyclic ring which may, in addition to the said nitrogen, contain a further nitrogen or an oxygen, and R¹ is alkylene of 2 to 10 carbon atoms. The said radicals and rings may be substituted by groups which are inert under the reaction conditions, e.g., alkyl or alkoxy each of 1 to 4 carbon atoms.

The following cycloalkenes are examples of suitable starting materials II: 1-morpholino-5-oximino-cyclopent-1-ene, 1-morpholino-6-oximino-cyclohex-1-ene, 1-morpholino-7-oximino-cyclohept-1-ene, 1-morpholino-8-oximino-cyclooct-1-ene, 1-morpholino-9-oximino-cyclonon-1-ene, 1-morpholino-10-oximino-cyclodec-1-ene, 1-morpholino-12-oximino-cyclododec-1-ene, 1-morpholino-18-oximino-cyclooctadec-1-ene, 1-morpholino-16-oximino-cyclohexadec-1-ene, 1-morpholino-17-oximinocycloheptadec-1-ene, 1-morpholino-15-oximino-cyclopentadec-1-ene, 1-morpholino-14-oximino-cyclotetradec-1-ene, 1-morpholino-11-oximinocycloundec-1-ene and 1-morpholino-13-oximino-cyclotridec-1-ene; analogous 1-piperidino-, 1-pyrrolidino-, 1-piperazino-, 1-dimethylamino-, 1-diethylamino- 1-N-methyl-N-ethylamino-, 1-imidazolidino-, 1-pyrrolino-(Δ2')- and 1-imidazolo-oximino compounds; 1-di-(methyl)-, 1-di(ethyl)-, 1-di-(n-propyl)-, 1-di-(isopropyl)-, 1-di-(n-butyl)-, 1-di-(isobutyl)-, 1-di-(sec.-butyl), 1-di-(tert.-butyl)-, 1-di-(pentyl), 1-di-(pentyl-2)-, 1-di-(pentyl-3)-, 1-di-(n-hexyl)-, 1-di-(n-heptyl)-, 1-di-(n-octyl)-, 1-di-(n-nonyl)-, 1-di-(n-decyl)-, 1-di-(2-ethylhexyl)-, 1-di-(2,2,6-trimethyl-n-pentyl)-, 1-di-(2-ethylpentyl)-, 1-di-(3-ethylpentyl)-, 1-di-(2,3-dimethyl-n-butyl)-, 1-di-(2,2-dimethyl-n-butyl)-, 1-di-(2-methylpentyl)-, 1-di-(3-methylpentyl)-, 1-di-(2,2,4-trimethylpentyl)-, 1-di-(2-methylheptyl)-, 1-di-(3-methylheptyl)-, 1-di-(4-methylheptyl), 1-di-(3-ethylhexyl)-, 1-di-(2,2-dimethylhexyl)-, 1-di-(2,3-dimethylhexyl)-, 1-di-(2,4-dimethylhexyl)-, 1-di-(2,5-dimethylhexyl)-, 1-di-(3,3-dimethylhexyl)-, 1-di-(3,4-dimethylhexyl)-, 1-di-(2-methyl-3-ethylpentyl)-, 1-di-(3-methyl-3-ethylpentyl)-, 1-di-(2,2,3-trimethylpentyl)-, 1-di-(2,2,4-trimethylpentyl)-, 1-di-(2,3,3-trimethylpentyl)-, 1-di-(2,3,4-trimethylpentyl)-, 1-di-(2,2,3,3-tetramethylbutyl)-oximino compounds; and corresponding oximino compounds which contain 2 of the above radicals which are, however, different from one another, e.g. the methylethyl-oximino compound.

The reaction is carried out with hydrazine, which in general is added in the form of hydrazine hydrate to the starting mixture. However, it is also possible to use hydrazine itself or its salts, e.g., the primary or secondary sulfates. The reaction is carried out with hydrazine in stoichiometric amount or, preferably, in from 1.1-fold to 1.5-fold excess, based on the starting material. If the starting mixture still contains oxygen, the amount of hydrazine is advantageously increased appropriately.

The reaction is in general carried out at from 20° to 200° C, preferably from 30° to 90° C, under atmospheric or superatmospheric pressure, and batchwise or continuously. Examples of suitable solvents are aromatic hydrocarbons, e.g., toluene, ethylbenzene, o-xylene, m-xylene, p-xylene, isopropylbenzene and methylnaphthalene, halohydrocarbons, especially chlorohydrocarbons, e.g., amyl chloride, cyclohexyl choride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, tetrachloroethane, trichloroethane, trichloroethylene, pentachloroethane, o-difluorobenzene, m-difluorobenzene, p-difluorobenzene, 1,2-dichloroethane, 1,1-dichloroethane, n-propyl chloride, 1,2-cis-dichloroethylene, n-butyl chloride, sec.-butyl chloride, tert.-butyl chloride, isobutyl chloride, chlorobenzene, fluorobenzene, bromobenzene, iodobenzene, o-dichlorobenzene, p-dichlorobenzene, m-dichlorobenzene, o-dibromobenzene, p-dibromobenzene, m-dibromobenzene, o-chlorotoluene, m-chlorotoluene, p-chlorotoluene, 1,2,4-trichlorobenzene, 1,10-dibromodecane and 1,4-dibromobutane, alkanols and cycloalkanols, e.g., ethanol, n-butanol, isobutanol, tert.-butanol, cyclohexanol, propanol and methanol, ethers, e.g., ethyl propyl ether, methyl tert.-butyl ether, n-butyl ethyl ether, di-n-butyl ether, diisoamyl ether, dioxane, diisopropyl ether, anisole, phenetole, cyclohexyl methyl ether, diethyl ether, tetrahydrofuran and thioanisole; aliphatic or cycloaliphatic hydrocarbons, e.g. heptane, pinane, nonane, o-, m- and p-cymene, gasoline fractions of boiling range from 70° to 190° C, cyclohexane, methylcyclohexane, petroleum ether, decalin, pentane, hexane, naphtha, 2,2,4-trimethylpentane, 2,2,3-trimethylpentane, 2,3,3-trimethylpentane, octane and appropriate mixtures. The amount of solvent used is advantageously from 200 to 10,000% by weight, preferably from 200 to 1,000% by weight, based on starting material II.

The reaction can be carried out as follows: hydrazine hydrate is slowly added to a solution of the starting material II and the mixture is kept at the reaction temperature for from 2 to 6 hours, e.g., is heated under reflux. The end product is then isolated in the conventional manner, e.g., by distilling the mixture and, if appropriate, recrystallizing the residue from one of the above solvents.

The compounds which may be manufactured by the process of the invention, especially the triazine derivative described in Example 1, have antiphlogistic properties and are valuable starting materials for the manufacture of dyes and pharmaceuticals. The antiphlogistic action of the triazine derivatives was tested on the carrageenin-induced paw oedema in rats. The test substances, administered orally, reduce the inflammatory swelling brought about by sub-plantar injection of 0.1 ml of a 1 percent strength carrageenin solution. The compounds I are valuable starting materials for the manufacture of other pesticides used, e.g., against scab, phytophthora infectans, powdery mildew and aquatic weeds, and in combating weeds in Indian corn, vine, sugar cane, millet and cotton crops. End products I which are particularly suitable for this type of use are those where $R^1$ has the above preferred meaning, and especially those obtained from the individual starting materials II mentioned as being particularly suitable.

In the Example which follows, parts are by weight and bear the same relation to parts by volume as that of the kilogram to the liter.

EXAMPLE 2,3,5,6,7,8-Hexahydro-1,2,4-benzotriazine-4-oxide-spiro-(3,1')-[oximino-(2')-cyclohexane]

6.5 parts of hydrazine hydrate are added to 25 parts of 1-morpholino-6-oximino-cyclohex-1-ene in 65 parts by volume of ethanol and the mixture is heated under reflux for 2 hours. A further 25 parts of 1-morpholino-6-oximino-cyclohex-1-ene in 65 parts by volume of ethanol are then added and the reaction mixture is heated under reflux for one hour. After cooling and concentrating the mixture, 23.2 parts (yield, 73% of theory) of 2,3,5,6,7,8-hexahydro-1,2,4-benzotriazine-4-oxide-spiro-(3,1')-[oximino-(2')-cyclohexane] of melting point 174° C (after recrystallization from ethanol) are obtained.

We claim:
1. 1,2,4-Dihydrotriazine-4-oxide-spiro-(3,1')-[oximino-(2')-cycloalkanes] of the formula

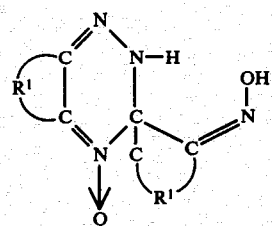

I, where $R^1$ is an alkylene of 2 to 10 carbon atoms.

2. A process for the manufacture of an 1,2,4-dihydrotriazine-4-oxide-spiro-(3,1')-[oximino-(2')-cycloalkane] of the formula

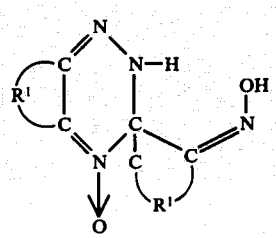

I, where $R^1$ is an alkylene of 2 to 10 carbon atoms, wherein the said radicals may be substituted by alkyl or alkoxy each of 1 to 4 carbon atoms, in which oximino-cycloalk-1-enes, which are substituted in the 1-position, of the formula

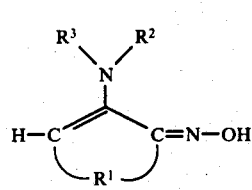

II, where $R^2$ and $R^3$ are identical or different and each is an alkyl of 1 to 8 carbon atoms or $R^2$ and $R^3$ together with the adjacent nitrogen are members of a 5-membered or 6-membered heterocyclic ring which may, in addition to the said nitrogen, contain a further nitrogen or an oxygen, wherein the said radicals and rings may be substituted by alkyl or alkoxy each of 1 to 4 carbon atoms, and $R^1$ has the above meaning, are reacted with hydrazine in organic solvents which are inert under the reaction condition.

3. A process as set forth in claim 1, in which the reaction is carried out with hydrazine in from 1.1-fold to 1.5-fold excess, based on the starting material.

4. A process as set forth in claim 1, in which the reaction is carried out at from 20° to 200° C.

5. A process as set forth in claim 1, in which the reaction is carried out at from 30° to 90° C.

6. A process as set forth in claim 1, in which the reaction is carried out in the presence of a solvent in amounts of from 200 to 10,000% by weight, based on starting material II.

7. A process as set forth in claim 1, in which the reaction is carried out in the presence of an aromatic hydrocarbon, halohydrocarbon, alkanol, cycloalkanol, ether or aliphatic or cycloaliphatic hydrocarbon.

* * * * *